United States Patent
Li et al.

(10) Patent No.: US 10,184,826 B2
(45) Date of Patent: Jan. 22, 2019

(54) IMAGING SYSTEM FOR GENERATING VIBRATION REGION CAUSED BY ULTRASOUND WAVE THEREBY TO OBTAIN OPTICALLY-SECTIONED IMAGES

(71) Applicant: NATIONAL TAIWAN UNIVERSITY, Taipei (TW)

(72) Inventors: Pai-Chi Li, Taipei (TW); Pei-Yu Chao, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 15/642,022

(22) Filed: Jul. 5, 2017

(65) Prior Publication Data
US 2018/0235474 A1 Aug. 23, 2018

(30) Foreign Application Priority Data
Feb. 21, 2017 (TW) .............................. 106105747 A

(51) Int. Cl.
| | |
|---|---|
| *G01H 9/00* | (2006.01) |
| *A61B 5/00* | (2006.01) |
| *A61B 8/00* | (2006.01) |
| *A61B 8/08* | (2006.01) |
| *G01N 21/49* | (2006.01) |

(Continued)

(52) U.S. Cl.
CPC .......... *G01H 9/008* (2013.01); *A61B 5/0082* (2013.01); *A61B 5/0097* (2013.01); *A61B 8/4444* (2013.01); *A61B 8/485* (2013.01); *G01N 21/1717* (2013.01); *G01N 21/45* (2013.01); *G01N 21/4795* (2013.01); *G01N 21/49* (2013.01); *G01N 29/00* (2013.01); *G01N 2021/479* (2013.01)

(58) Field of Classification Search
CPC ..... A61B 8/485; A61B 5/0097; A61B 5/0095; A61B 5/0082; G01H 9/00; G01H 9/008; G01H 9/002; G01N 29/041; G01N 29/043; G01S 15/8972
See application file for complete search history.

(56) References Cited

U.S. PATENT DOCUMENTS

| | | | | |
|---|---|---|---|---|
| 5,212,667 A | * | 5/1993 | Tomlinson, Jr. ...... | A61B 5/0059 367/11 |
| 5,293,873 A | * | 3/1994 | Fang .................... | A61B 5/0091 600/437 |

(Continued)

*Primary Examiner* — Michael P LaPage
(74) *Attorney, Agent, or Firm* — Muncy, Geissler, Olds & Lowe, P.C.

(57) ABSTRACT

An imaging system is configured for generating vibration region caused by ultrasound wave thereby to obtain a plurality of optically-sectioned images. In the imaging system, a stage is operable to be moved along a plurality of scanning imaging positions, and applied to deposit an object with at least one scattering material. When the object receives an ultrasound wave, a shear wave is generated to displace the scattering material thereby to form a vibration region. A laser generating device is configured to transmit a laser beam, which penetrates the vibration region to form a speckle pattern and focused at a focusing position. An optical imaging device is set at the focusing position to receive the laser beam to generate a plurality of scanning optically-sectioned images with respect to the scanning imaging positions.

4 Claims, 4 Drawing Sheets

(51) Int. Cl.
*G01N 29/00* (2006.01)
*G01N 21/17* (2006.01)
*G01N 21/45* (2006.01)
*G01N 21/47* (2006.01)

(56) References Cited

U.S. PATENT DOCUMENTS

| | | | | |
|---|---|---|---|---|
| 6,041,248 A | * | 3/2000 | Wang | G01N 21/4795 |
| | | | | 600/407 |
| 2004/0127782 A1 | * | 7/2004 | Sfez | A61B 5/0048 |
| | | | | 600/407 |
| 2007/0187632 A1 | * | 8/2007 | Igarashi | A61B 5/0048 |
| | | | | 250/559.36 |
| 2010/0125205 A1 | * | 5/2010 | Park | A61B 5/0095 |
| | | | | 600/443 |
| 2012/0182561 A1 | * | 7/2012 | Masumura | A61B 5/0095 |
| | | | | 356/601 |
| 2014/0009808 A1 | * | 1/2014 | Wang | G02F 1/33 |
| | | | | 359/10 |
| 2014/0081102 A1 | * | 3/2014 | Baym | A61B 5/0097 |
| | | | | 600/328 |
| 2014/0114188 A1 | * | 4/2014 | Sangawa | G01S 15/8972 |
| | | | | 600/437 |
| 2015/0029819 A1 | * | 1/2015 | Yacoubian | G01N 21/171 |
| | | | | 367/7 |
| 2018/0140279 A1 | * | 5/2018 | Perrey | A61B 8/485 |

* cited by examiner

IMAGING SYSTEM FOR GENERATING VIBRATION REGION CAUSED BY ULTRASOUND WAVE THEREBY TO OBTAIN OPTICALLY-SECTIONED IMAGES

This application claims the benefit of Taiwan Patent Application Serial No. 106105747, filed Feb. 21, 2017, the subject matter of which is incorporated herein by reference.

BACKGROUND OF INVENTION

1. Field of the Invention

The present invention is related to an imaging system for generating vibration region caused by ultrasound wave to obtain optically-sectioned images, and more particularly is related to an imaging system for generating vibration region caused by ultrasound wave to obtain optically-sectioned images and processing these images to generate the elasticity image.

2. Description of the Prior Art

With the development of technologies, the improvement of medical technologies may increase the lifespan of humans. In many diseases, such as cancer, stiff nodules were formed in the biological tissue. For this reason, palpation was widely used in clinical physical examinations for sensing the degree and distribution of the stiffness of biological tissues. However, the palpation technique is highly relied on the experience of the doctor or the physician and the probability of using such technique for discovering early stage of a disease may be low. Therefore, there is a need for improving the sensitivity and specificity of the stiffness-sensing technique for accurately identifying the pathological region.

During past decades, there has been an intensive development of noninvasive imaging techniques for characterizing the stiffness of biological tissue. These techniques, such as non-invasive elasticity imaging based on ultrasound, have been exploited in numerous clinical applications, including the detection of prostate cancer, breast cancer, and the staging of liver fibrosis.

However, the imaging sensitivity and resolution of the current imaging techniques still require improvements in order to provide better contrast and distinguishable elasticity imaging result. Thus, there exist the needs to improve the conventional technology.

SUMMARY OF THE INVENTION

The common problem of the conventional elasticity imaging techniques is that the imaging resolution is still relatively poor, and elasticity distribution of the tissue may not be accurately reconstructed. Accordingly, an imaging system for generating vibration region caused by ultrasound wave to obtain a plurality of optically-sectioned images is provided in the present invention, which uses the ultrasound wave to generate a vibration region on the object to be detected, moves the object along a plurality of scanning imaging positions to generate images corresponds to the scanning imaging positions, and processes these images to generate the elasticity image so as to achieve three-dimensional elasticity detection by using the optically-sectioned images.

Accordingly, the main objective of the present invention is to provide an imaging system for generating vibration region caused by ultrasound wave to obtain a plurality of optically-sectioned images. The imaging system comprises an ultrasound device, a translational stage, a laser generating device, an optical focusing device, and an optical imaging device. The ultrasound device is utilized for transmitting an ultrasound wave onto an investigating region within the object. The translational stage is at least partially located in the investigating region and is operable to be moved to a plurality of scanning imaging positions on a moving path. The translational stage is utilized for carrying and locating an object contains at least one scattering material. When the ultrasound wave is delivered into the object, a shear wave is generated in the object to vibrate at least one scattering material so as to form a vibration region in the object. The laser generating device is utilized for transmitting a laser beam along a beam propagation path. When the laser beam penetrates the object contains at least one scattering material, and onto the optical imaging device, at least one speckle pattern is imaged. The optical focusing device is located on the beam propagation path to focus the laser beam, which penetrated the object, at a focusing position, and an aperture is used to partially block the light from out-of-focusing position. The optical imaging device is set at the focusing position to receive the laser beam so as to generate a plurality of scanning optically-sectioned images corresponding to the scanning imaging positions, wherein at least one of the scanning optically-sectioned images shows the at least one speckle pattern. The optical imaging device may contain processing unit for reconstructing the elasticity image of the object from plurality of scanning optically-sectioned images.

In accordance with an embodiment of the imaging system for generating vibration region caused by ultrasound wave to obtain a plurality of optically-sectioned images of the present invention, the reduced scattering coefficient of the scattering material is required to be greater than 0.2 cm$^{-1}$. The aperture of the optical focusing device has a plurality of hole diameters, which can be used for adjusting the required interval between the scanning positions.

In accordance with an embodiment of the imaging system for generating vibration region caused by ultrasound wave to obtain a plurality of optically-sectioned images of the present invention, the imaging system for generating vibration region caused by ultrasound wave to obtain a plurality of optically-sectioned images further comprises a beam expansion device. The beam expansion device is located on the beam propagation path between the laser generating device and the translational stage, for expanding the illumination region of the laser beam. The beam expansion device is a combination of a concave lens and a convex lens. In addition, the optical focusing device comprises an aperture stop and at least two lenses. The aperture on the aperture stop partially allows the light beam to pass. The at least two lenses are located on the either side of the aperture stop along the beam propagation path, for adjusting the focusing position.

In accordance with an embodiment of the imaging system for generating vibration region caused by ultrasound wave to obtain a plurality of optically-sectioned images of the present invention, the imaging system for generating vibration region caused by ultrasound wave to obtain a plurality of optically-sectioned images further comprises a control device, which is electrically connected to the ultrasound device and the optical imaging device, for controlling the driving sequence for ultrasound device to transmit the ultrasound wave and optical imaging device to record optical image of the object, so as to adjust the effective frame rate of the imaging system. If the effective frame rate is high, the propagation speed of the shear wave can be accurately detected such that the error in the stiffness estimation of the high elasticity object can be reduced.

By using the imaging system for generating vibration region caused by ultrasound wave to obtain a plurality of optically-sectioned images provided in the present invention, which uses the ultrasound wave to generate the vibration region on the object to be detected, moves the object along a plurality of scanning imaging positions to generate images corresponding to the scanning imaging positions, and processes these images to generate the elasticity image, thereby, the elasticity distribution of the object can be reconstructed effectively by using the sectioned images. The ability to detect stiff nodule accurately is helpful and convenient for both research and practical applications.

BRIEF DESCRIPTION OF THE DRAWINGS

The present invention will now be specified with reference to its preferred embodiment illustrated in the drawings, in which.

DESCRIPTION OF THE PREFERRED EMBODIMENT

There are various embodiments of the imaging system for generating vibration region caused by ultrasound wave to obtain a plurality of optically-sectioned images provided in accordance with the present invention, which are not repeated hereby. Only one preferred embodiment is mentioned in the following paragraph as an example.

Figure 1:
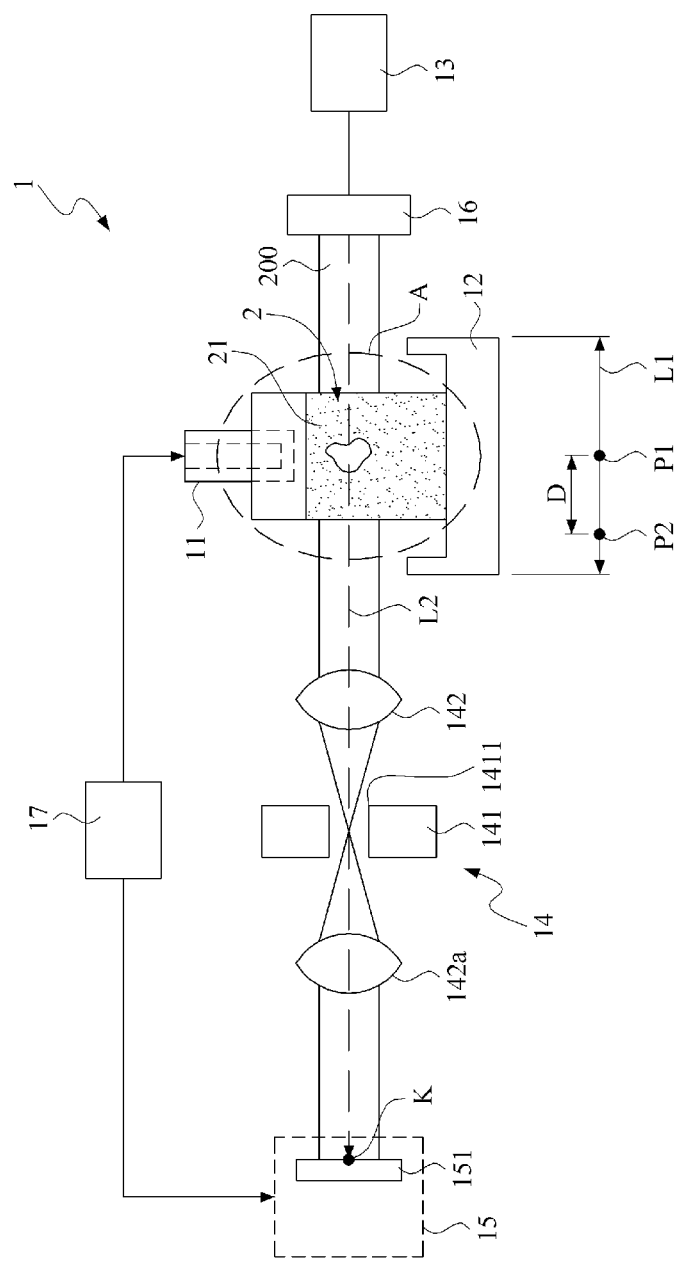
FIG. 1 is a schematic view of an imaging system for generating vibration region caused by ultrasound wave to obtain a plurality of optically-sectioned images in accordance with a preferred embodiment of the present invention.
Figure 1A:
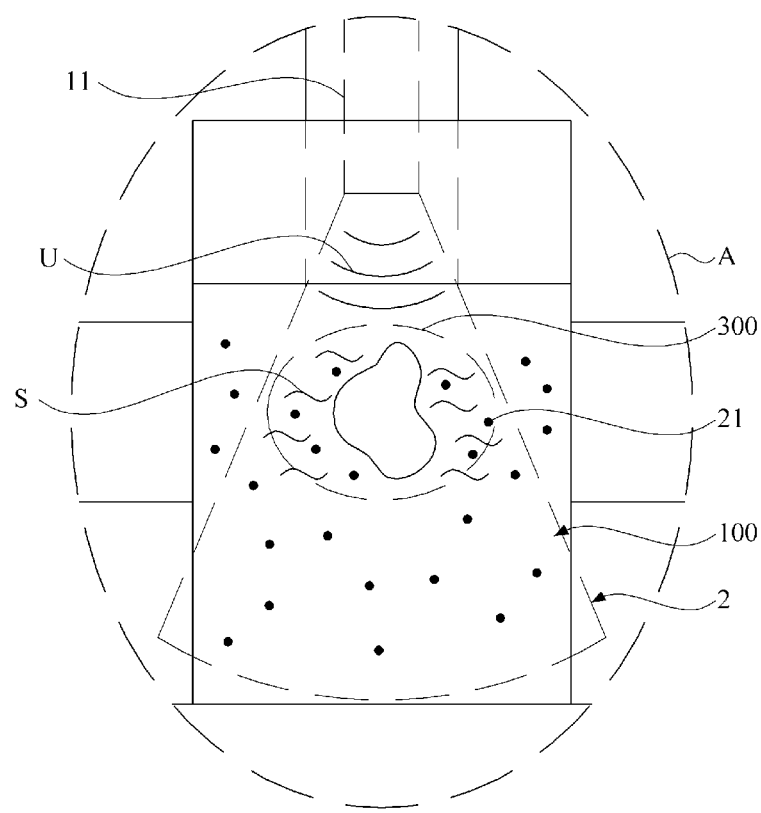
FIG. 1A is a partially enlarged view of FIG. 1.

Please refer to FIG. 1 and FIG. 1A, wherein FIG. 1 is a schematic view of an imaging system for generating vibration region caused by ultrasound wave to obtain a plurality of optically-sectioned images in accordance with a preferred embodiment of the present invention, and FIG. 1A is a partially enlarged view of FIG. 1.

As shown, the imaging system 1 for generating vibration region caused by ultrasound wave to obtain a plurality of optically-sectioned images in accordance with a preferred embodiment of the present invention (hereinafter the "imaging system") comprises an ultrasound device 11, a translational stage 12, a laser generating device 13, an optical focusing device 14, an optical imaging device 15, and a beam expansion device 16.

The ultrasound device 11 can be an existing ultrasound probe, which is utilized for transmitting an ultrasound wave U to an investigating region 100. The investigating region 100 is defined as the combination of the spaces to which the ultrasound wave can be transmitted. Concretely speaking, the aforementioned space is the depth of field of the ultrasound device, which includes the focusing point of the ultrasound device. The investigating region is the space where acoustic radiation force is induced from the transmitted ultrasound wave, which thereby generates a shear wave.

The translational stage 12 is at least partially located in the range of the investigating region 100. The translational stage 12 is operable to be moved to a plurality of scanning imaging positions P1 and P2 on a moving path L1, and is utilized for carrying and locating an object 2 to be detected which includes at least one scattering material 21. In accordance with a preferred embodiment of the present invention, the object 2 can be placed in a transparent container (the container can be omitted in other embodiments, and the transparent container can be made from glass or acrylic), and the object 2 to be detected can be any biological tissue or 3D cell culture structure, and the reduced scattering coefficient of the scattering material 21 (such as the light scattering particles), which causes the object to be semitransparent, is required to be greater than $0.2$ $cm^{-1}$ for producing the necessary speckle pattern. In the preferred embodiment of the present invention, the reduced scattering coefficient is $0.97$ $cm^{-1}$ as an example. It should be mentioned that the reduced scattering coefficient of the container should be smaller than that of the scattering material 21, however, if the thickness of the container is ranged between 1 and 2 millimeters, the reduced scattering coefficient of the scattering material 21 is not limited to the aforementioned value. In addition, a moving path L1 along the X-axis is provided in the present preferred embodiment as an example, the moving path can be expanded to include 2D or 3D movement.

In addition, if the object 2 is a 3D cell culture structure, the object 2 is required to be in solid phase for allowing the shear wave to propagate therein. The ingredient of the object may be the biological hydrogel or extracellular matrix gel (i.e. Matrigel and collagen), and the biological tissue or cells to be cultured are placed in the extracellular matrix gel.

The laser generating device 13 can be any existing device that can generate and transmit laser beams, and is utilized for transmitting a laser beam 200 along a beam propagation path L2. The optical focusing device 14 has an aperture 1411 located on the beam propagation path L2. Concretely speaking, the optical focusing device 14 in accordance with the preferred embodiment of the present invention includes a aperture stop 141 and at least two lenses 142 and 142a, the aperture stop 141 has the aforementioned aperture, and the two lenses 142 and 142a are located on the beam propagation path L2.

The optical imaging device 15 is located on the beam propagation path L2. The optical imaging device 15 may include the optical lenses, optical sensing unit 151 (i.e. charge-coupled device (CCD), the complementary metal-oxide-semiconductor (CMOS) or any existing optical sensor), and the image processer depends on the design in practice.

The beam expansion device 16 is located on the beam propagation path L2 between the translational stage 12 and the laser generating device 13. The beam expansion device 16 can be a combination of a concave lens and a convex lens, a combination of two convex lenses, or a diffuser, depends on the design in practice. The beam expansion device 16 is utilized for expanding the coverage of the laser beam 200.

Figure 2:
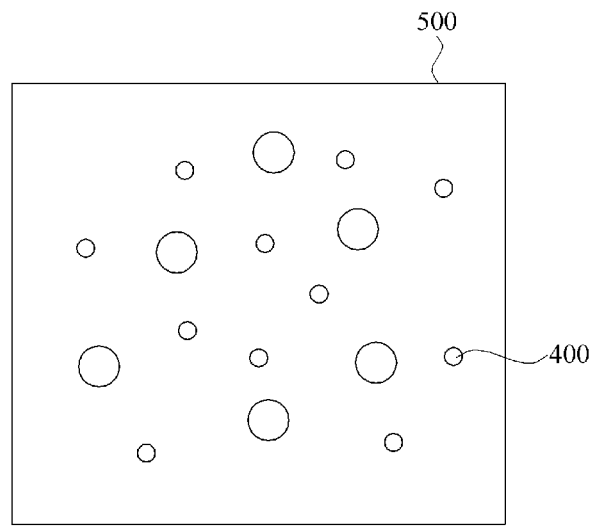
FIG. 2 and FIG. 3 are schematic views of the scanning optically-sectioned images in accordance with a preferred embodiment of the present invention.
Figure 3:
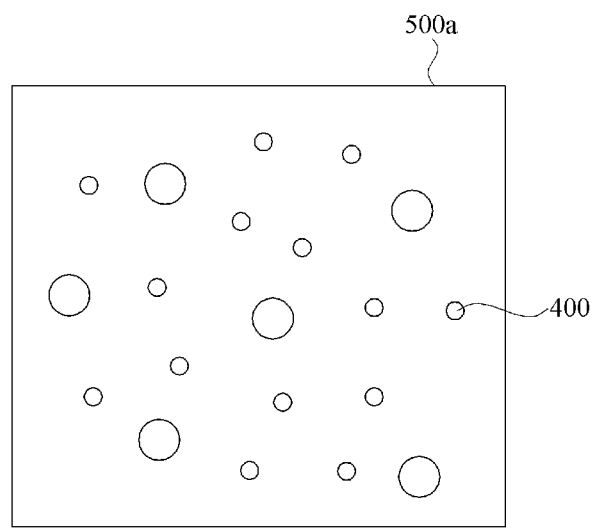
Figure 4:
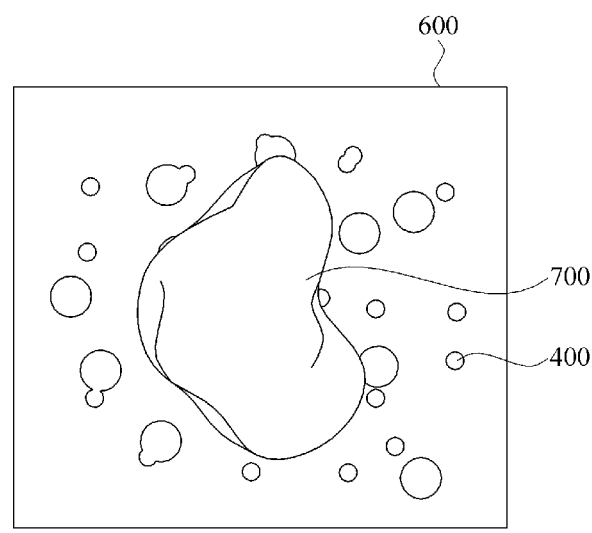
FIG. 4 is a schematic view of the elasticity image in accordance with a preferred embodiment of the present invention.

Please refer to FIG. 1 to FIG. 4, wherein FIG. 2 and FIG. 3 are schematic views of the scanning optically-sectioned images in accordance with a preferred embodiment of the present invention, and FIG. 4 is a schematic view of the elasticity image in accordance with a preferred embodiment of the present invention.

As shown, when the object 2 to be detected receives the ultrasound wave U, a shear wave S is generated in the object 2 to vibrate the at least one scattering material 21 so as to form a vibration region 200 in the object 2. In the vibration region 200, the shear wave S may cause the scattering particles in the object to displace and change the refractive index of the object. The laser beam 200 propagating along the beam propagation path L2 may generate at least one a speckle pattern 400 after penetrating the vibration region 300 (as shown in FIG. 2 and FIG. 3), and the laser beam 200 is then focused at a focusing location K on the beam propagation path L2 after the laser beam 200 penetrating the vibration region 300 and the aperture 1411 in a serial. The aforementioned optical sensing unit 151 is located at the focusing position K.

In the present preferred embodiment, the laser beam 200 penetrates the vibration region 300, the lens 142, the aperture 1411, and the lens 142a, and consequently focused at the focusing position K. The position of the lenses 142 and the 142 can be used for adjusting the focusing position K. In addition, the aperture 1411 can be used for shielding the unwanted illumination (i.e., the unwanted portion of the expanded laser beam 200 is shielded), adjusting the thickness of the focusing plane. In the present preferred embodiment, the aperture 1411 has been adjusted in advance to show a fixed hole diameter and also a fixed focusing plane.

The optical imaging device 15 is set at the focusing position K to receive the laser beam 200 so as to generate a plurality of scanning optically-sectioned images 500 and 500a corresponding to the scanning imaging positions P1 and P2. For example, for the scanning imaging position P1, the optical imaging device 15 receives the scanning optically-sectioned image 500, for the scanning imaging position P2, the optical imaging device receives the scanning optically-sectioned image 500a, and at least one of these scanning optically-sectioned images shows the at least one speckle pattern 400.

The optical imaging device 15 may process these scanning optically-sectioned images 500 and 500a to form a 3D elasticity image 600. Concretely speaking, the optical imaging device 15 may process the scanning optically-sectioned images 500 and 500a as two 2D elasticity images then recombine the scanning optically-sectioned images 500 and 500a to rebuild the 3D elasticity image. The elasticity image 600 includes the speckle pattern 400 and the image 700 of the object (such as the integration of the background image and the image of the object to be detected). It should be also noted that the images shown in FIG. 2 to FIG. 4 are merely the schematic views.

It should be also mentioned that although only two scanning optically-sectioned images 500, 500a and two scanning imaging positions P1, P2 are mentioned in the present preferred embodiment, but in practice, more scanning optically-sectioned images and scanning imaging positions can be used, and thus the present invention is not so restricted.

In addition, transmission of the shear wave S may cause displacement of scattering particles in the object 2 to be detected. When the laser beam 200 passes through the vibration region 300, phase of the laser beam would be changed, which resulted in a change of the interference pattern (i.e. the speckle pattern). The image formed by the optical imaging device 15 would show the changed in the interference pattern as local blurring. Therefore, the wave front of the shear wave S can be detected by measuring the spatial blurring of the speckle pattern 400. The time difference between the shear wave S wave front at any two locations along the shear wave S propagation path can be used to yield the velocity of the shear wave S, and the velocity of the shear wave S is related to the elasticity of the object 2.

In addition, in the present preferred embodiment, a scanning gap D is the distance between the neighboring scanning imaging positions P1 and P2, the aperture 1411 of optical focusing device 14 has a plurality of hole diameters (i.e. the aperture 1411 is operable to be expanded or shrunk), thereby the scanning gap D can be adjusted according to the size of the hole diameters. For example, by using a small hole diameter with a small scanning gap D, the precision of the estimated propagation speed of the shear wave S can be enhanced. In addition, a smaller hole diameter of the aperture 1411 may increase the size of the speckle pattern 400 and block the multi-scattering light waves exiting from the object 2, so as to enhance the contrast and clarity of the speckle pattern 400 in the scanning optically-sectioned images 500 and 500a.

In addition, the imaging system 1 may also include a control device 17, which is electrically connected to the ultrasound device 11 and the optical imaging device 15, and is also electrically connected to the translational stage 12. The control device 17 can be used for controlling the time sequence, for example, when the translational stage 12 is moved to a certain position, the control device 17 would control the driving sequence for the ultrasound device 11 to transmit the ultrasound wave U and also control the driving sequence of the optical imaging device 15, such as control the optical imaging device 15 to acquire N images, such that, the optical imaging device 15 may identify the condition of the shear wave S propagated on the image focusing plane according to the aforementioned N images, and then the control device 17 may control the translational stage 12 to move to the next position and repeat the aforementioned steps.

In accordance with another embodiment of the present invention, for example, after the translational stage 2 is moved to the scanning imaging position P1, the control device 17 controls the ultrasound device 11 to transmit the ultrasound wave U, and controls the optical imaging device 15 to take a real-time image. Thereafter, the control device 17 will control the ultrasound device 11 to transmit the ultrasound wave U again, and controls the optical imaging device 15 to acquire another real-time image after a time delay. The aforementioned process can be repeated for different scanning imaging position. Therefore, the control device 17 is utilized for controlling whether the cycle of the ultrasound wave U transmitted by the ultrasound device 11 is synchronized with the imaging cycle or not, which depends on the need in practice, and the wave speed of the shear wave S can be calculated thereby. It should be noted that the control device 17 may also control the exposure time of the optical imaging device 15.

For example, after the control device 17 triggers the ultrasound device 11, the control device 17 may wait for 100 microseconds before sending the triggering signal to the optical imaging device 15, and the optical imaging device 15 would take the image showing the condition after the shear wave S has been propagated for 100 microseconds, i.e. the position of the shear wave S wave front after the shear wave S has been induced and propagated for 100 microseconds. The propagation of the shear wave S can be fully detected by modulating the delay time between two trigger signals. If the adjustable interval of the delay time is 100 microseconds, the effective imaging frame rate of the shear wave S would be 10000 frames/second.

In conclusion, by using the imaging system for generating vibration region caused by ultrasound wave to obtain a plurality of optically-sectioned images provided in the present invention, 3D elasticity image can be reconstructed by utilizing technical features of the laser generating device, the translational stage, the optical focusing device, and the optical imaging device. In addition, because the optical scanning system is used, the contrast of the elasticity image and the sensitivity can be effectively enhanced.

While the present invention has been particularly shown and described with reference to a preferred embodiment, it will be understood by those skilled in the art that various changes in form and detail may be without departing from the spirit and scope of the present invention.

What is claimed is:

1. An imaging system configured for generating a vibration region caused by an ultrasound wave to obtain a plurality of optically-sectioned images, comprising:
   an ultrasound device, utilized for transmitting an ultrasound wave to an investigating region;
   a translational stage, at least partially located in the investigating region, operable to be moved to a plurality of scanning imaging positions on a moving path, and being utilized for locating an object with at least one scattering material, wherein when the object receives the ultrasound wave, a shear wave is generated in the object to vibrate the at least one scattering material so as to form a vibration region in the object;
   a laser generating device, utilized for transmitting a laser beam along a beam propagation path to have the laser beam penetrate the vibration region to form at least one a speckle pattern; an optical focusing device, having an aperture on the beam propagation path, to focus the laser beam which penetrated the object at a focusing position on the beam propagation path after penetrating the vibration region and the aperture; and
   an optical imaging device, set at the focusing position to receive the laser beam so as to generate a plurality of scanning optically-sectioned images with respective to the scanning imaging positions and process the scanning optically-sectioned images as 2D elasticity images and combine the 2D elasticity images to build a 3D elasticity image, wherein at least one of the scanning optically-sectioned images shows the at least one speckle pattern;
   wherein the optical imaging device comprises an optical lens, an optical sensing unit and an image processer; and
   wherein a scanning gap is located between the neighboring scanning imaging positions, the aperture of the optical focusing device is set with a plurality of hole diameters, and the scanning gap is adjusted according to the hole diameters.

2. The imaging system of claim 1, further comprising a beam expansion device, which is located on the beam propagation path between the translational stage and the laser generating device, for expanding illumination region of the laser beam.

3. The imaging system of claim 2, wherein the beam expansion device is a combination of a concave lens and a convex lens.

4. The imaging system of claim 1, wherein the optical focusing device comprises:
   an aperture stop, containing an aperture that partially allows the laser beam to pass; and
   at least two lenses, located on the beam propagation path of the two sides of the aperture stop, for adjusting the focusing position.

* * * * *